United States Patent [19]

Lippert et al.

[11] Patent Number: 5,334,759
[45] Date of Patent: Aug. 2, 1994

[54] PREPARATION OF FORMIC ACID FROM CARBON MONOXIDE AND WATER

[75] Inventors: Ferdinand Lippert, Bad Duerkheim; Arthur Hoehn, Ludwigshafen, both of Fed. Rep. of Germany

[73] Assignee: BASF Aktiengesellschaft, Ludwigshafen, Fed. Rep. of Germany

[21] Appl. No.: 107,054

[22] Filed: Aug. 17, 1993

[30] Foreign Application Priority Data

Aug. 19, 1992 [DE] Fed. Rep. of Germany ....... 4227394

[51] Int. Cl.$^5$ .................... C07C 53/02; C07C 53/04; C07C 53/06
[52] U.S. Cl. .................................................. 562/609
[58] Field of Search ......................................... 562/609

[56] References Cited

FOREIGN PATENT DOCUMENTS 248259 9/1987 European Pat. Off. .

Primary Examiner—Jose' G. Dees
Assistant Examiner—Joseph M. Conrad, III

Attorney, Agent, or Firm—Keil & Weinkauf

[57] ABSTRACT

A process for the preparation of formic acid by the reaction of carbon monoxide with water at temperatures of from 100° to 250° C. and absolute from 100 to 350 bar, in which tertiary amines of the general formula I

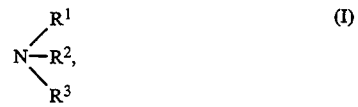

in which $R^1$, $R^2$, $R^3$ individually denote $C_1$–$C_{14}$ alkyl, $C_3$–$C_8$ cycloalkyl, aryl, and $C_7$–$C_{16}$ aralkyl or together denote a 1,4-alkylene group or 1,5-alkylene group optionally mono- to tetra-substituted by $C_1$–$C_4$ alkyl, provided that the total number of carbon atoms in $R^1$, $R^2$, and $R^3$ is from 3 to 40, are added to the reaction mixture.

4 Claims, No Drawings

PREPARATION OF FORMIC ACID FROM CARBON MONOXIDE AND WATER

The present invention relates to a process for the preparation of formic acid from carbon monoxide and water in the presence of tertiary amines.

EP-A 248,259 discloses the preparation of formic acid from carbon monoxide and water in a two-stage process, in which primary or secondary hydroxyalkylamine is carbonylated with carbon monoxide in the first stage, and the hydroxylalkyl formamide thus formed is hydrolyzed to form formic acid and amine in the presence of an acid catalyst in the second stage. The formic acid is removed from the hydrolysis mixture by stripping with steam under pressure. The aqueous formic acid obtained is then dried by azeotropic distillation using diisopropyl ether or a formate as entraining agent. The hydrolysis of the formamide in the second stage is unsatisfactory, however. On the one hand, there is achieved a maximum degree of hydrolysis of only 45% (cf Table 2, page 10), the hydrolysis temperatures being between 70° and 150° C., and on the other hand the hydrolysis proceeds only very slowly. The residence times are between 4 and 20 h.

DE-A 3,903,664 describes the synthesis of formic acid from carbon monoxide and water in the presence of tertiary hydroxyalkylamines. The corresponding formates are formed from the carbon monoxide and the tertiary hydroxyalkylamines as intermediates. The preparation of the formates is carried out under relatively mild conditions, but a maximum conversion of only 22% is achieved. The subsequent hydrolysis with equimolar amounts of water gives a quantitative yield. However, only low space-time yields are achieved (cf Example 1: STY=22.1 g of HCOOH/L.h; Example 2: STY=21 g of HCOOH/L.h). The aqueous formic acid solution is worked up as described in EP-A 248,259.

It is thus an object of the present invention to overcome the aforementioned drawbacks.

Accordingly, we have found a novel and improved process for the preparation of formic acid by the reaction of carbon monoxide with water at temperatures of from 100° to 250° C. and absolute pressure of from 100 to 350 bar, wherein a tertiary amine of the general formula I

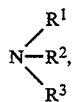
(I)

in which

R$^1$, R$^2$, R$^3$ individually denote C$_1$–C$_{14}$ alkyl, C$_3$–C$_8$ cycloalkyl, aryl, and C$_7$–C$_{16}$ aralkyl or together denote a 1,4-alkylene group or 1,5alkylene group optionally mono- to tetra-substituted by C$_1$–C$_4$ alkyl, provided that the total number of carbon atoms in R$^1$, R$^2$, and R$^3$ is from 3 to 40, is added to the reaction mixture.

The process of the invention may be carried out as follows:

Water and the tertiary amine I, which preferably has aliphatic, araliphatic and/or aromatic radicals, can be placed in a vessel in the liquid phase and carbon monoxide then introduced under pressure. The reaction between carbon monoxide and water can be carried out in the presence of the tertiary amine batchwise or, preferably, continuously at temperatures of from 100° to 250° C. and preferably from 150° to 200° C. and absolute pressures of from 100 to 350 bar and preferably from 200 to 300 bar.

Carbon monoxide can be fed to the reaction as pure substance or as synthesis gas. The molar ratio of water to the amine can be varied within wide limits, and suitable molar ratios are from 0.2:1 to 100:1 and preferably from 20:1 to 1:1, more preferably from 10:1 to 2:1.

Suitable reactors are boilers, bubble-cap columns or trickle-bed towers. The isolation of the formic acid from the reaction mixture can be effected by conventional separating methods such as distillation or stripping. The thermal separation of such ammonium formates into formic acid and free amine is disclosed, e.g., in EP-A 1432.

The substituents R$^1$, R$^2$, and R$^3$ in compounds I have the following meanings:

R$^1$, R$^2$, R$^3$
  C$_1$–C$_{14}$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isoctyl, n-nonyl, isononyl, n-decyl, isodecyl, n-undecyl, isoundecyl, n-dodecyl, and isododecyl and preferably C$_1$–C$_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably C$_1$–C$_4$ alkyl such as methyl, ethyl, n-propyl, isopropyl, n-butyl, isobutyl, sec-butyl, and tert-butyl.

C$_3$–C$_8$ cycloalkyl such as cyclopropyl, cyclobutyl, cyclopentyl, cyclohexyl, cycloheptyl, and cyclooctyl and preferably cyclopentyl, cyclohexyl, and cyclooctyl, aryl such as phenyl, 1-naphthyl, 2-naphthyl, 1-anthryl, 2-anthryl, and 9-anthryl and preferably phenyl, 1-naphthyl, and 2-naphthyl and more preferably phenyl, C$_7$–C$_{16}$ aralkyl and preferably C$_7$–C$_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl and more preferably benzyl, 1-phenethyl, and 2-phenethyl, or the pairs R$^1$ and R$^2$, R$^1$ and R$^3$, or R$^2$ and R$^3$
  each denote a 1,4-alkylene group or 1,5-alkylene group optionally mono- to tetra-substituted by C$_1$–C$_4$ alkyl, provided that the total number of carbon atoms in R$^1$, R$^2$, and R$^3$ in compounds I is from 3 to 40, such as in —(CH$_2$)$_4$—, —(CH$_2$)$_5$—, —CH(CH$_3$)—CH$_2$—CH$_2$—, —CH$_2$—CH(CH$_3$)—CH$_2$—, and is preferably from 4 to 24 and more preferably from 6 to 18.

Particularly suitable tert-alkylamines are N-triethylamine, N-tributylamine, N-tripentylamine, N-trihexylamine, N-triheptylamine, N-trioctylamine, dimethyltetradecylamine, diethyltetradecylamine, dimethyloctylamine, and diethyloctylamine, as well as N,N'-dimorpholinoethane or N-hexylmorpholine.

EXAMPLES

EXAMPLE 1

In a Hastelloy HC-4 autoclave having a capacity of 0.3 L and equipped with a magnetic stirring unit there were placed 50.6 g (0.5 mol) of triethylamine and 90 g (5 mol) of water. The autoclave was sealed and carbon monoxide was forced in until the inside pressure reached 50 bar. The reactor was then heated to 200° C. and pressurized to 300 bar with carbon monoxide. Following a period of one hour, the autoclave was cooled and the liquid effluent analyzed. 12.4 g (0.27 mol) of formic acid were found, which is equivalent to a conversion rate of 54%, based on the amine used. The space-time yield was 41 g of formic acid/L.h.

EXAMPLE 2

In a similar manner, 50.6 g (0.5 mol) of triethylamine and 90 g (5 mol) of water were caused to react for 5 h at 200° C. under an over-all pressure of 200 bar. The effluent contained 20.7 g (0.45 mol) of formic acid, which is equivalent to a conversion rate of 90% based on amine used and to a space-time yield of 14 g of formic acid/L.h.

EXAMPLE 3

Example 2 was repeated using an over-all pressure of 250 bar. 21.4 g (0.46 mol) of formic acid were formed, which is equivalent to a conversion rate of 93%, based on the triethylamine used.

EXAMPLE 4

81 g (0.8 mol) of triethylamine and 72 g (4 mol) of water were placed in an HC-autoclave having a capacity of 0.3 L and stirred at 200° C. under a pressure of 300 bar. Over a period of about 2 h, 12.8 g (0.28 mol) of formic acid were produced, which is equivalent to a conversion rate of 35% based on triethylamine and to a space-time yield of 21.3 g of formic acid/L.h.

We claim:

1. A process for the preparation of formic acid by the reaction of carbon monoxide with water at temperature of from 100° to 250° C. and absolute pressures of from 100 to 350 bar, wherein a tertiary amine of the formula I

in which

R$^1$, R$^2$, R$^3$ individually denote C$_1$–C$_{14}$ alkyl, C$_3$–C$_8$ cycloalkyl, aryl, and C$_7$–C$_{16}$ aralkyl or together denote a 1,4-alkylene group or 1,5-alkylene group optionally mono- to tetra-substituted by C$_1$–C$_4$ alkyl, provided that the total number of carbon atoms in R$^1$, R$^2$, and R$^3$ is from 3 to 40, is added to the reaction mixture.

2. A process for the preparation of formic acid by the reaction of carbon monoxide with water as defined in claim 1, wherein the total number of carbon atoms in R$^1$, R$^2$, and R$^3$ is from 4 to 20.

3. A process for the preparation of formic acid by the reaction of carbon monoxide with water as defined in claim 1, wherein the tertiary amines I used are triethylamine, trihexylamine, triheptylamine, trioctylamine, dimethyltetradecylamine, N-hexylmorpholine, or N,N'-dimorpholinoethane.

4. A process for the preparation of formic acid as defined in claim 1, wherein the molar ratio of water to tertiary amine is from 20:1 to 1:1.

* * * * *